(12) United States Patent
Hamel et al.

(10) Patent No.: US 7,846,150 B2
(45) Date of Patent: Dec. 7, 2010

(54) APPARATUS AND METHOD FOR SYNCHRONIZING A WIRELESS REMOTE CONTROL TO A CENTRAL CONTROL UNIT SO AS TO ALLOW REMOTE CONTROL OF A MEDICAL DEVICE OVER A SECURE WIRELESS CONNECTION

(75) Inventors: Andrew J. Hamel, San Mateo, CA (US); Michael G. Hilldoerfer, Mountain View, CA (US); Brannon P. Wells, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 642 days.

(21) Appl. No.: 11/263,083

(22) Filed: Oct. 31, 2005

(65) Prior Publication Data

US 2006/0116667 A1    Jun. 1, 2006

Related U.S. Application Data

(60) Provisional application No. 60/623,949, filed on Nov. 1, 2004.

(51) Int. Cl.
*A61B 17/00* (2006.01)
(52) U.S. Cl. .......................... 606/1; 600/126
(58) Field of Classification Search ............. 606/1, 606/34, 101; 600/118, 471, 126; 607/60; 709/223, 224; 128/920; 340/825.72
See application file for complete search history.

(56) References Cited

U.S. PATENT DOCUMENTS

| | | | |
|---|---|---|---|
| 6,074,388 A * | 6/2000 | Tockweiler et al. | 606/34 |
| 2002/0156466 A1 | 10/2002 | Sakurai et al. | |
| 2003/0093103 A1 * | 5/2003 | Malackowski et al. | 606/170 |
| 2003/0093503 A1 | 5/2003 | Yamaki et al. | |
| 2005/0049458 A1 * | 3/2005 | Honda et al. | 600/118 |
| 2005/0080403 A1 * | 4/2005 | Takahashi | 606/1 |
| 2005/0143724 A1 | 6/2005 | El-Galley et al. | |

(Continued)

FOREIGN PATENT DOCUMENTS

CA    2 353 016    1/2002

(Continued)

OTHER PUBLICATIONS

U.S. Appl. No. 10/607,810, Applicants: Andrew J. Hamel, et al., filed Jun. 27, 2003 entitled Foot-Operated Control Console for Wirelessly Controlling Medical Devices.

(Continued)

*Primary Examiner*—Michael Peffley
*Assistant Examiner*—Ronald Hupczey, Jr.
(74) *Attorney, Agent, or Firm*—Flynn, Thiel, Boutell & Tanis, P.C.

(57) ABSTRACT

A system for controlling one or more medical devices by a remote console. The remote console communicates wirelessly with a central control unit that connects to one or more of the medical devices. To minimize the possibility that a medical device will be activated by a stray or unauthorized wireless command signal, the central control unit must synchronize with the remote console and establish a secure communication link with it before the central control unit will respond to a wireless command signal transmitted by the remote console.

27 Claims, 12 Drawing Sheets

U.S. PATENT DOCUMENTS

2006/0047199 A1    3/2006    Miyazawa

FOREIGN PATENT DOCUMENTS

EP        1 629 786 A2    3/2006

OTHER PUBLICATIONS

U.S. Appl. No. 11/025 652, Applicant: Andrew J. Hamel, filed Dec. 29, 2004 entitled System for Remotely Controlling Two or More Medical Devices.

HERMES™ Operating Room Control Center, Operating & Maintenance Manual, Stryker® Endoscopy, May 1999.

"FDA Approval of Additional Devices for Computer Motion's HERMES Control Center", Medical Robotics Updates, TeleMed-E-Zine, Jul. 1999, vol. 2 Issue 7.

Karl Storz Communication Bus (SCB), EndoWorld, Nov. 1999.

International Preliminary Report on Patentability mailed May 10, 2007.

* cited by examiner

FIG. 8

Definition of Terms

BS – Base Station

BS_ACK – Base Station Acknowledge Packet

BS_BIND1 – Base Station Bind 1 Packet

BS_BIND2 – Base Station Bind 2 Packet

BS_BREAK – Base Station Break Connection Packet

BS_MOVEREQ – Base Station Move Request Packet

CDMA – Code Division Multiple Access

CHKSM – Checksum

DPID – Data Path Identifier

FS – Footswitch

FS_REBIND – Footswitch Rebind Packet

FS_STATUS – Footswitch Status Packet

FS_ACK – Footswitch Acknowledge Packet

MID – Manufacturer's Identification Number

MID0 – 1$^{st}$ Byte of MID

MID1 – 2$^{nd}$ Byte of MID

MID2 – 3$^{rd}$ Byte of MID

MID3 – 4$^{th}$ Byte of MID

PCKID0 – Packet Identifier, bit 0

PCKID1 – Packet Identifier, bit 1

PCKID2 – Packet Identifier, bit 2

PN Code – Code used by the WUSB transceiver to encode and decode data.

RFID – Radio Frequency Identification. 125 kHz inductively coupled data storage and retrieval system consisting of a small integrated circuit, or tag, used to store data, and a transceiver which writes and reads data to and from the tag via the modulation of a magnetic field in which the tag is located.

WUSB – Wireless Universal Serial Bus. Marketing designation for Cypress 2.4GHz Wireless Low-Level Protocol.

PACKET STRUCTURE

| PCKID | Description | DATA |
|---|---|---|
| FS_ACK | Used to reply to BS packets during binding | None |
| FS_STATUS | Used to reply to BS_ACK packets during normal operation | Current pedal and switch states of the footswitch |
| FS_REBIND | Used to reconnect to a BS that the FS has been synced to. | None |
| BS_ACK | Used to tell the FS that a STATUS report is requested | None |
| BS_BIND1 | Used during the bind process, provides the first half of the BS MID to the FS | BS_MID (B0, B1) |
| BS_BIND2 | Used during the bind process, provides the second half of the BS MID to the FS | BS_MID (B2, B3) |
| BS_BREAK | Used to notify the FS that the connection is being severed | None |
| BS_MOVEREQ | Used to request a footswitch moves channels AND/OR changes the PNCode it is using. | New Channel and New PNCode |

PACKET TYPES

FIG. 10

| Packet from WUF Receiver (BS) | DIR | Packet from WUF Footswitch (FS) |
|---|---|---|
| BS_BIND1 | → | |
| BS_BIND2 | → | |
| | ← | FS_ACK |
| BS_MOVEREQ | → | |
| | ← | FS_ACK |

NOT BOUND Binding Procedure

FIG. 11

| Packet from WUF Receiver (BS) | DIR | Packet from WUF Footswitch (FS) |
|---|---|---|
| BS_ACK or BS_MOVEREQ or BS_BREAK | → | |
| | ← | FS_STATUS |

BOUND Console Pedal and Switch State Communication

FIG. 12

| Packet from WUF Receiver (BS) | DIR | Packet from WUF Footswitch (FS) |
|---|---|---|
| BS_ACK | → | |
| | ← | FS_REBIND |
| BS_ACK | → | |
| | ← | FS_STATUS |

WAS BOUND Rebinding Procedure

FIG. 13

PACKET TIMING DIAGRAM

APPARATUS AND METHOD FOR SYNCHRONIZING A WIRELESS REMOTE CONTROL TO A CENTRAL CONTROL UNIT SO AS TO ALLOW REMOTE CONTROL OF A MEDICAL DEVICE OVER A SECURE WIRELESS CONNECTION

CROSS REFERENCE TO RELATED APPLICATION

This application claims the benefit of U.S. Provisional Application No. 60/623,949, filed Nov. 1, 2004.

FIELD OF THE INVENTION

An apparatus and method for controlling one or more medical devices by a wireless remote console, and, in particular, an apparatus and method for establishing a secure wireless connection between a wireless remote console and a central control unit so as to prevent the medical device from responding to unauthorized signals generated by another wireless device.

BACKGROUND OF THE INVENTION

Endoscopy is a technology that allows minimally-invasive viewing of internal features of a body. In medicine, endoscopy allows acquisition of high-quality images of internal features of a human body without the need for invasive surgery. The basic tool of endoscopy is the endoscope ("scope"), which is inserted into the body to be viewed. Some endoscopic procedures involve the use of a flexible scope, as in the medical field of gastroenterology, for example. Other medical procedures, such as arthroscopy or laparoscopy, use a rigid scope. The scope is normally coupled to a high-intensity light source that transmits light into the body through the scope, and to a camera head that includes electronics for acquiring video image data. The camera head is typically coupled to a video monitor, which displays video images acquired by the camera.

In endoscopic surgery, various other medical devices may be used, such as an insufflator to pump pressurized gas into body cavities to create more space for viewing and working, an electrocautery tool to stop bleeding, and/or various tools to cut or shape body tissues. These devices are typically controlled remotely by means such as foot pedals and/or switches placed on the floor of the operating room, which are operated by the surgeon. The foot controls may control functions such as on/off, speed or intensity, direction of movement of the tool, mode of operation, etc. The use of foot controls and the like allows the surgeon to adjust various modes and settings of the tools (e.g., speed, intensity) himself, without having to put a tool down, change hands, touch potentially contaminated surfaces with his hands, or take his eyes off the patient.

First generation foot pedals and other types of remote controls typically functioned by relaying command signals, in the form of electrical impulses, over a conductive line or cable that physically connected the remote control to the device being controlled. As technology advanced, the remote controls became wireless, thereby allowing a remote control to be located anywhere within the operating room without having to run a cable along the floor.

Although the use of wireless remote controls within a medical environment, such as an operating room, is advantageous, it also introduces additional variables and risks that could ultimately endanger a patient. For instance, stray electromagnetic signals from other devices within the vicinity give rise to the risk of a controlled device improperly responding even though a command was never issued by the remote control. More importantly, in a given clinical environment, multiple wireless remote controls may be used in close proximity to each other, thereby introducing the risk of a receiver unit responding to control signals from the wrong remote control.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which:

FIG. 8 is a table containing a plurality of term definitions;

FIG. 10 is a table that lists each packet ID utilized with certain embodiments of the invention, what the packet ID is used for, and what specific data the packet ID contains;

FIG. 11 is a table that depicts the binding procedure that the remote console and central control unit go through;

FIG. 12 is a table that depicts the communication that occurs between a remote console and a central control unit that are bound together;

FIG. 13 is a table that depicts the rebinding procedures undertaken by a remote console and central control unit which have lost communication.

DETAILED DESCRIPTION

As described in greater detail below, a single wireless remote console in accordance with the invention (hereafter referred to simply as "console") allows a surgeon or other operator to control one or more medical devices during an endoscopic medical procedure. The console can comprise one or multiple controls designed for operation by an operator's hand or foot to control a medical device or devices. For illustrative purposes, consider an example of a wireless, foot-operated console that includes one or more foot pedals and/or foot switches to control one or more devices, including a selection switch to allow selection of the device to be controlled if multiple devices are connected. In response to operation of the foot controls, the console transmits signals wirelessly to a central control unit, which causes the central control unit to select a device to be controlled and to control the selected device. The foot control console may include a rechargeable battery, which may be sealed within the console's housing and charged inductively when the console is placed in a docking station. The receiver unit and the docking station can be separate units or they can be integrated within a single housing.

I. The Wireless Remote Console and Central Control Unit

Figure 1:
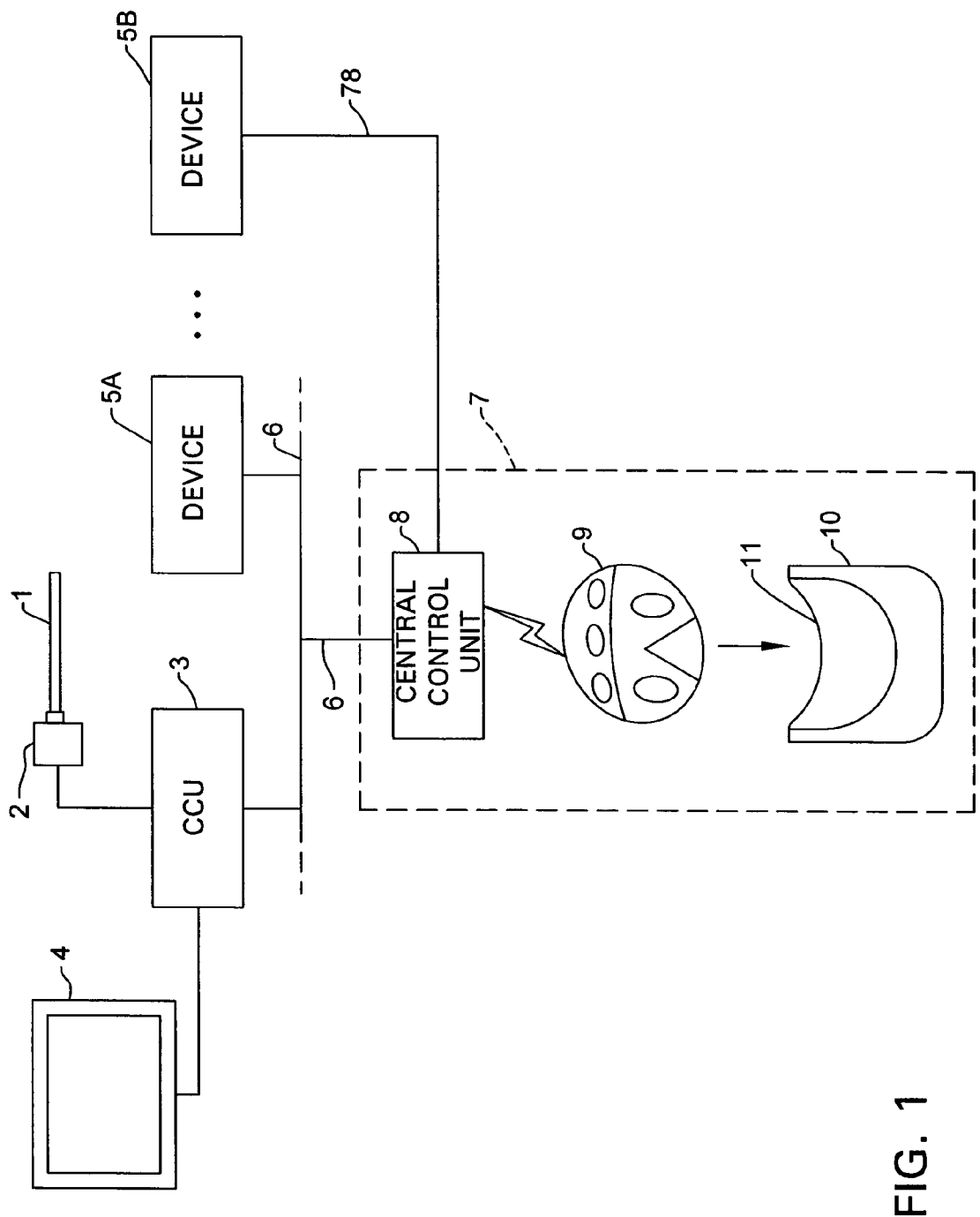
FIG. 1 is a block diagram of a wireless remote control system including a wireless remote console according to certain embodiments of the invention.

FIG. 1 illustrates one example of a wireless remote control system where the remote console 9 is represented by a wireless foot control apparatus in accordance with the invention. The system includes an endoscope 1 and a camera 2 coupled to the endoscope 1 and to a camera control unit (CCU) 3. Also coupled to the CCU 3 is a video monitor 4 to display images acquired by the camera 2. The system also includes a number of different supporting devices 5 (e.g., 5A, 5B, etc.), which may include devices ranging from surgical tools (i.e., an insufflator, an electrocautery tool, a radio frequency generator, or a cutter/shaver tool) to other devices utilized in a surgical or clinical environment (i.e., a video capture device, operating table lights and room lights). Depending on what they are, one or more of these supporting devices 5 may be able to connect to each other by a common wired communication medium 6, as are device 5A and the CCU 3. The wired communication medium 6 may be, for example, an IEEE standard 1394 backplane connection, an Ethernet connection, or other communication medium with similar capability.

Connecting to each of the devices 5, either directly or through the wired communication medium 6, is a central control unit 8. The remote console 9, represented in FIG. 1 as a wireless foot control apparatus, cooperates with the central control unit 8 to control any of the devices 5 connected to the central control unit 8. Specifically, in this example, console 9 includes various foot operated pedals, switches and/or other foot-operated controls which, when actuated by the operator, cause the console 9 to transmit control signals wirelessly to the central control unit 8. In response to control signals received from the console 9, the central control unit 8 communicates with one of the various devices 5 that is currently selected. This communication may occur over the wired communication medium 6, as would be the case with device 5A, or by a direct connection 78 (which may be analog or digital) to the central control unit 8, as would be the case with device 5B. The direct connection 78 may emulate the inputs of a remote control console specific to the device 5. Furthermore, one or more controlled devices 5 might communicate with the central control unit 8 only via a wireless link.

As the console 9 is wireless, it requires its own power source. According to one embodiment, this power source can be one or more replaceable alkaline batteries. In another embodiment, the power source comprises one or more rechargeable batteries that can be removed from the console 9 for recharging. Alternatively, the rechargeable battery or batteries can be sealed within the housing 27 of the console 9. In such an embodiment, the housing 27 can be made of molded plastic or other similar material, making the console 9 lightweight, durable, soakable, and easy to clean. This approach is desirable because, among other reasons, it is common during certain endoscopic surgical procedures for considerable amounts of water and/or other fluids to be spilled onto the floor of the operating room. A sealed console housing is advantageous, therefore, since there is no need for electrical contacts that are directly exposed to this operating room environment. In addition, the use of a rechargeable internal battery reduces the number of electrical cables needed in the operating room.

Figure 2:
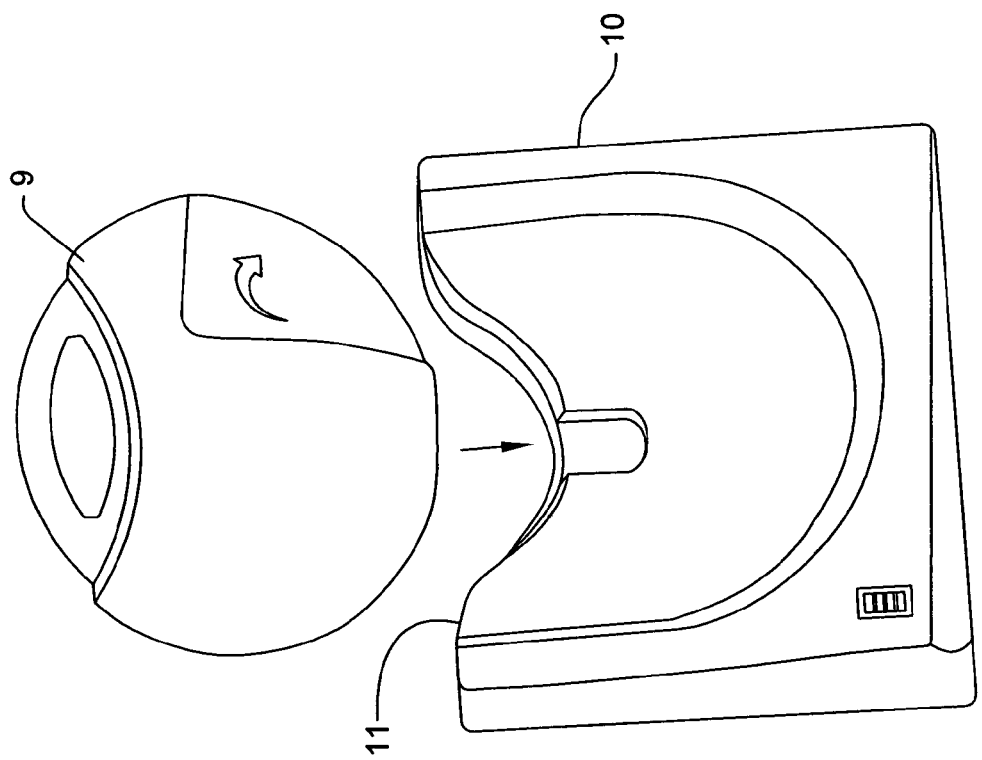
FIG. 2 shows the remote console and a docking station into which the console can be placed to recharge a battery in the wireless foot control apparatus.
Figure 3:
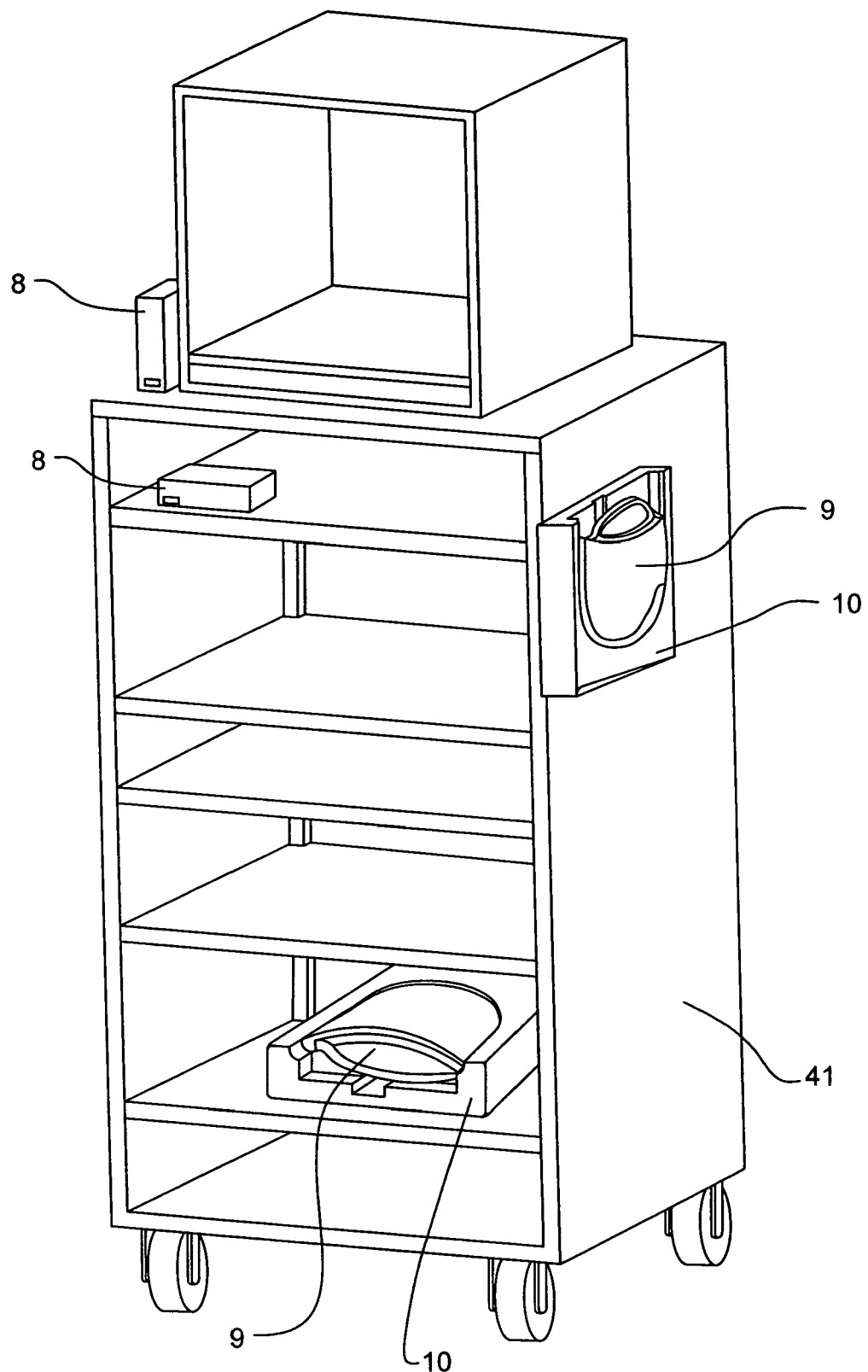
FIG. 3 shows how the docking station and the central control unit can be placed or mounted on an equipment cart.

To charge the internal battery, a docking station 10 may be provided. The console 9 is placed into the docking station 10, where the battery is charged by means such as electromagnetic induction. The docking station 10 also serves as a convenient holder for the console 9 when the console 9 is not in use. FIG. 2 shows one example of a docking station 10 and how the console 9 can be inserted into the docking station 10 for charging of the console's battery and/or for storage. FIG. 3 shows how a docking station 10 can be placed or mounted on an equipment cart 41 of the type typically used for endoscopic equipment.

Figure 4:
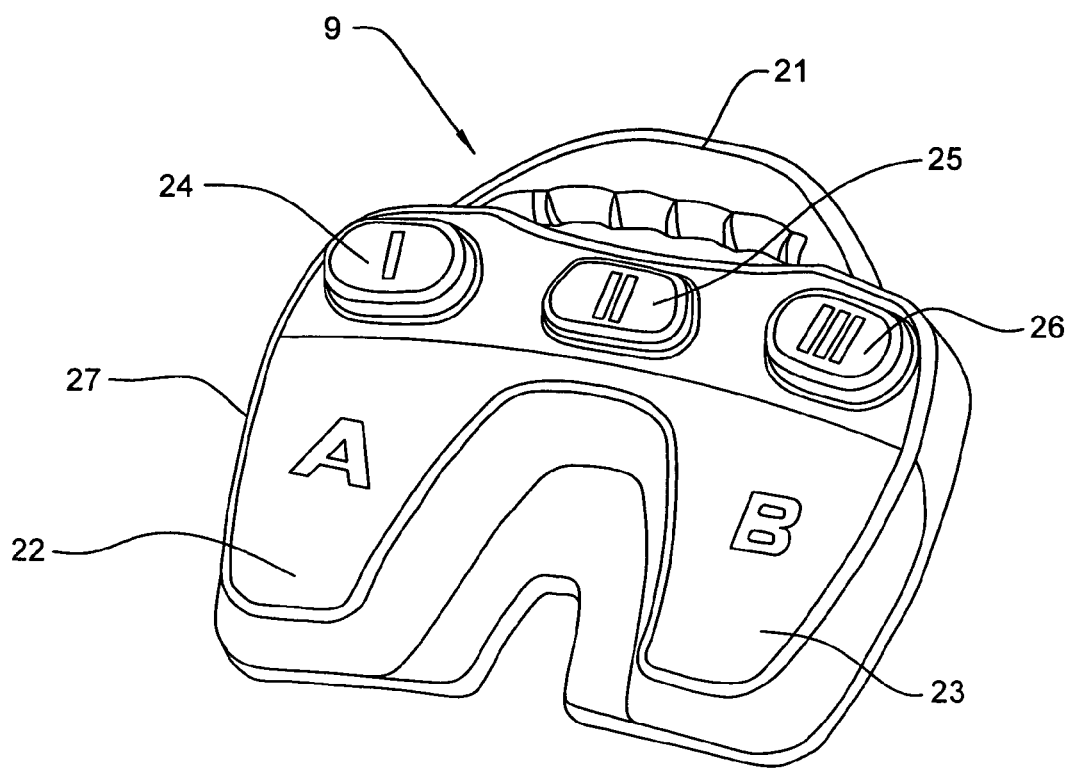
FIG. 4 shows an exterior view of remote console according to certain embodiments of the invention.

Depicted in the illustrative example of FIG. 4 is an exterior view of one possible type of remote console 9 that can be used in the present invention. Specifically, FIG. 4 depicts a foot-controlled console 9 which is relatively light in weight and includes a handle 21 that allows the console 9 to be conveniently picked up and carried by operating room staff. As shown, the console 9 includes left and right pedals 22 and 23, respectively, as well as three foot operated switches, i.e., a left switch 24, a middle switch 25, and a right switch 26. Other embodiments may include a different combination of pedals, switches, and/or other controls. The switches 24-26 may be, for example, simple pushbutton switches and may be used, for example, to select different modes of operation of the various devices 5. The pedals 22 and 23 may be simple potentiometer-type (variable displacement) foot controls, such as for use in controlling the speed, intensity, and/or other variable settings of a medical tool.

For the remainder of the detailed discussion, all references to console 9 will presume to mean a foot-controlled console 9 such as the example illustrated in FIG. 4. However, as previously mentioned, the wireless remote control system of the present invention is not limited to one type or design of wireless remote control console 9, but instead can be configured for use with virtually any type and design of console 9, including, but not limited to, both foot-operated and hand-operated consoles.

In certain embodiments, the console 9 of FIG. 4, while capable of controlling any of the devices 5, controls only one of the devices 5 at a time. In such embodiments, one of the switches 24-26 is used as a selection switch to allow the operator to select the device 5 to be controlled. The function of each of the other controls can vary depending upon which device 5 is currently selected to be controlled. The selection can be accomplished by simply pressing the designated selection switch repeatedly to cycle between the different available devices 5.

In other embodiments, the console 9 is capable of controlling two or more devices 5 simultaneously. For example, two or more separate switches and/or pedals can be used to control two or more separate devices 5 at the same time. Or, the same control on the console 9 might be used to control two or more devices.

The central control unit 8 will detect which devices 5 are present or connected to the wired communication medium 6 and/or by direct connection 78. Therefore, the console 9 does not need to have any knowledge of which device 5 is currently selected—such knowledge can be maintained entirely within the central control unit 8. The console 9 simply transmits generic control signals, which the central control unit 8 receives and translates into other control signals having the appropriate format and protocol for the currently selected device 5. In some embodiments, the central control unit 8 can receive input from multiple consoles 9 simultaneously and output the corresponding control signal to either one or multiple devices, depending on if the multiple consoles 9 are controlling the same device or multiple devices.

Figure 5:
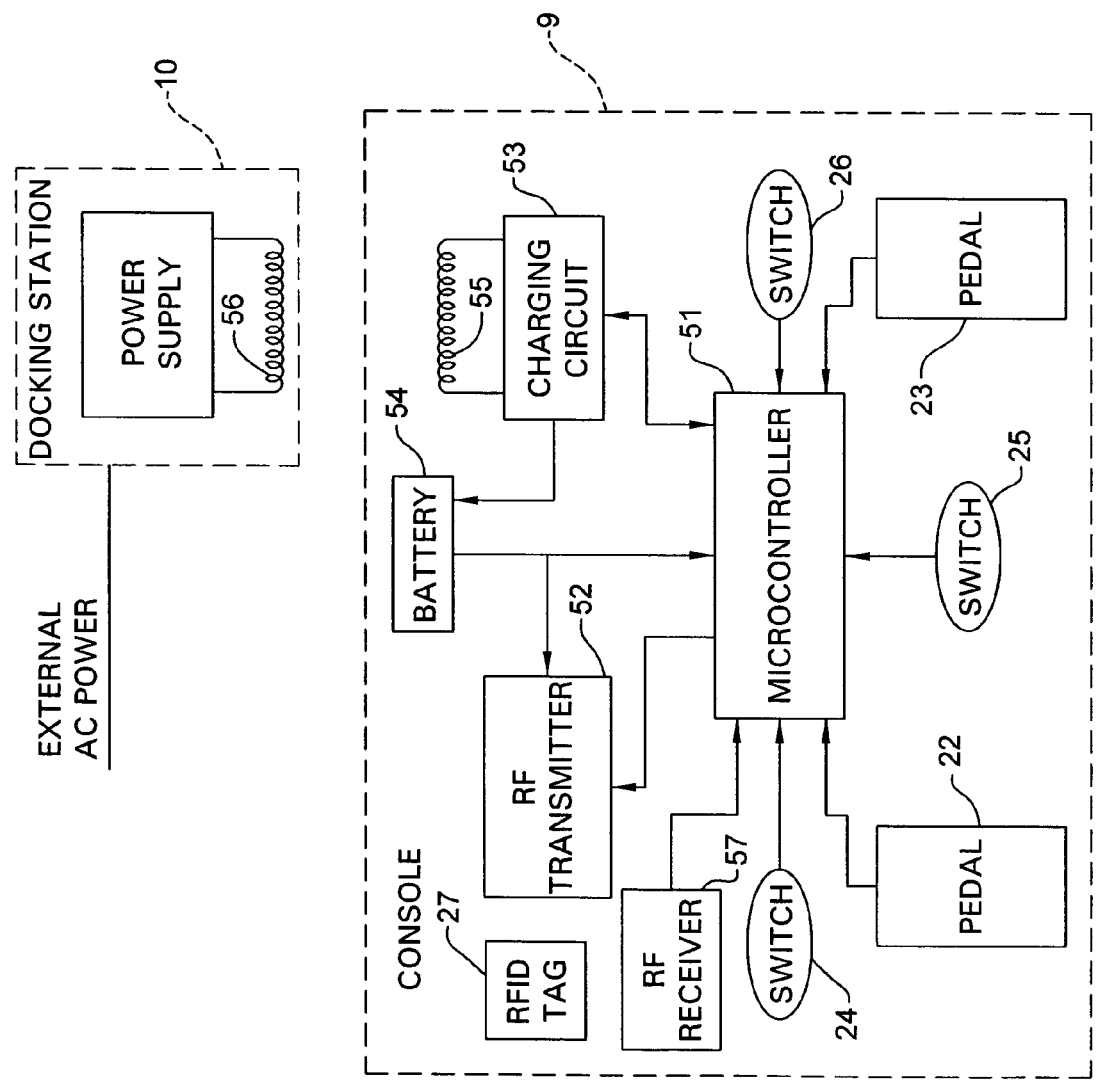
FIG. 5 is a block diagram of the remote console according to certain embodiments of the invention.

FIG. 5 shows the components of a console 9 according to one exemplary embodiment of the invention. As illustrated, the console 9 includes a conventional programmable microcontroller 51 which couples to a relatively short-range radio frequency (RF) transmitter 52 and RF receiver 57. The RF transmitter 52 and RF receiver 57 can be combined into a single transceiver unit such as, for example, the Cypress WUSB chip set which works within the 2.4 GHz ISM band. In accordance with other embodiments, the console 9 may employ alternate transceiver configurations that operate using other wireless protocols, including 900 MHz RF, Bluetooth, 802.11a/b/g, Ultra-Wide Band (UWB) and Zigbee, as well as non-RF based protocols such as infrared (IR) or laser.

Further included in the console 9 is at least one rechargeable battery 54 and an induction coil 55 coupled to a charging circuit 53, which, in turn, is coupled to the microcontroller 51. Also present is a radio frequency identification (RFID) chip or tag 27 that is either contained within the console 9, or alternatively, fixedly attached to the exterior surface of the console 9. The internal components of the console 9 (i.e., other than the switches and pedals) are completely sealed within the housing of the console 9, which protects those components from damage from the operating room environment and reduces the risk of electrical shock and sparks.

The microcontroller 51 can communicate with the RF transmitter 52 and RF receiver 57 through, for example, a standard RS-232 interface. The RF transmitter 52 transmits control signals to the central control unit 8, under the control of the microcontroller 51, in response to user inputs applied at the foot operated controls (switches and pedals).

The microcontroller 51 in each wireless console 9 is assigned a unique identification (ID) code. As will be discussed in greater detail below, this ID code allows the microcontroller 51 to uniquely identify all the command signals transmitted by the console 9 by incorporating its ID code into the signals it generates and subsequently passes on to the RF transmitter 52.

Figure 6:
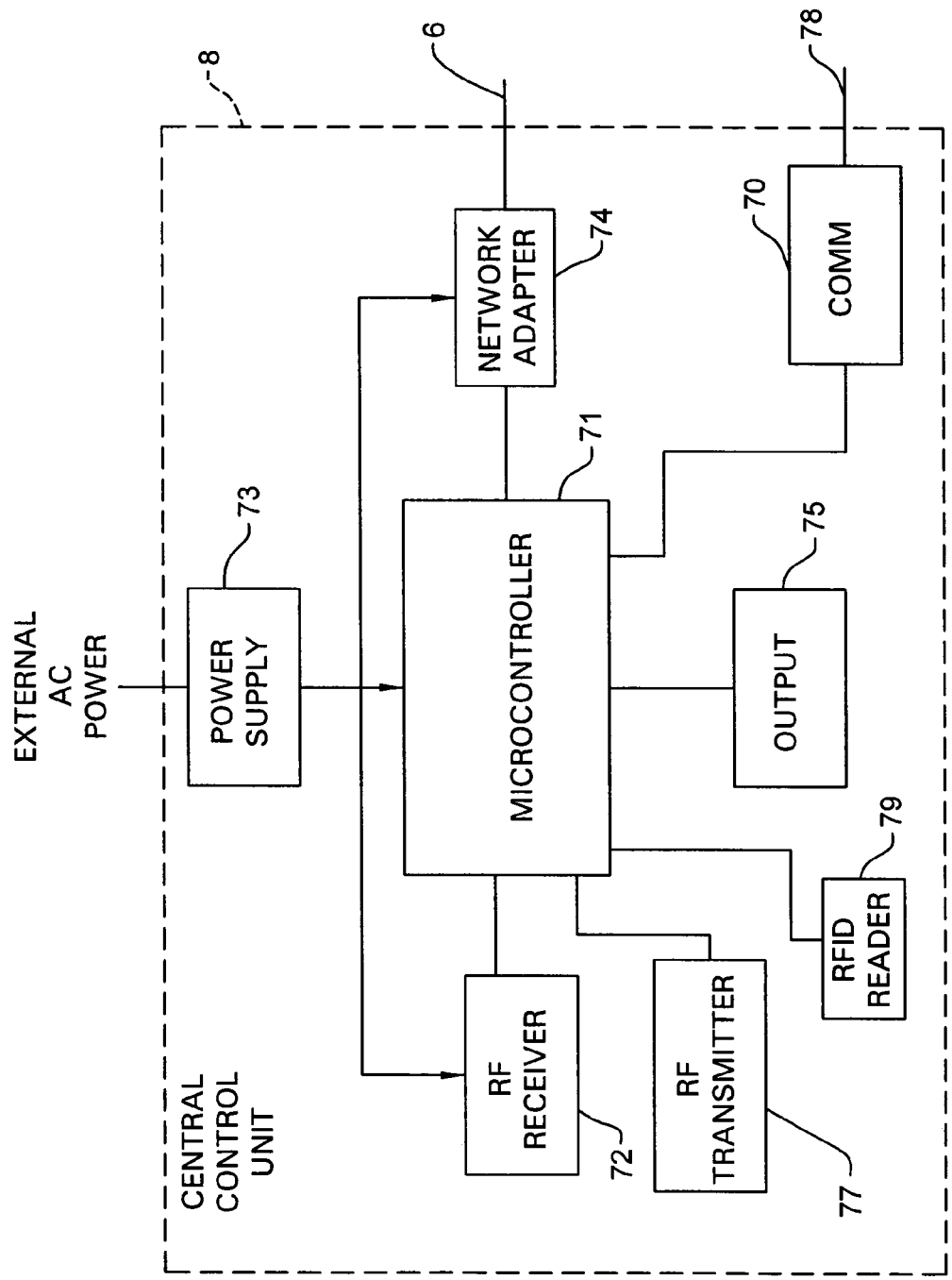
FIG. 6 is a block diagram of a central control unit according to certain embodiments of the invention.

FIG. 6 is a block diagram of the central control unit 8 according to one embodiment of the invention. As shown, the central control unit 8 includes a programmable microcontroller 71, a wireless receiver 72 and wireless transmitter 77 (or, alternatively, a combined transceiver), a power supply 73, a network adapter 74, and one or more output indicators 75. The microcontroller 71 controls the overall operation of the central control unit 8. The microcontroller 71 may, in other embodiments, be replaced by one or more other forms of control devices capable of performing the same role, such as a programmable general-purpose or special-purpose microprocessor, ASIC, etc. The wireless receiver 72 receives control signals transmitted from the console 9 as described above, while the wireless transmitter 77 dispatches signals from the central control unit 8 to the wireless console 9. The microcontroller 71 may communicate with the RF receiver 72 and RF transmitter 77, through various means, including, for example, a standard RS-232 interface. The power supply 73 provides regulated power for the central control unit 8, based on power supplied from any available external power source.

Also included within the central control unit 8 is a radio frequency identification (RFID) reader 79 which generates a relatively weak magnetic field. When an RFID tag is brought within close proximity to the RFID reader 79, the tag picks up the magnetic energy and begins communicating with the RFID reader 79. More specifically, the magnetic field being generated by the RFID reader 79 becomes uniquely modulated in a predetermined manner when a RFID tag is in close proximity. It is by this means of modulating a magnetic field that the RFID tag communicates information, such as an ID code, to the RFID reader 79.

The central control unit 8 also includes one or more output indicators 75 which are used to communicate various information to the user of the system, including indicating which device 5 (FIG. 1) is currently selected. The output indicator(s) 75 may include, for example, one or more light-emitting diodes (LEDs), liquid crystal displays (LCDs), audio speakers, or the like.

Depending upon which of the devices 5 is currently selected, the microcontroller 71 uses the control signals received by the wireless receiver 72 to generate commands and/or other control signals directed to a particular device 5 on the wired communication medium 6. The microcontroller 71 is programmed to generate specific commands or other control signals in a format and/or protocol that is appropriate for the currently selected device 5. The microcontroller 71 causes the network adapter 74 to transmit these generated commands onto the wired communication medium 6.

The network adapter 74 can be, for example, a standard IEEE standard 1394 adapter, while the wired communication medium 6 is, for example, an IEEE 1394 backplane. In that case, the central control unit 8 can use standard IEEE 1394 protocols to identify the other devices that are connected to the backplane. In still other embodiments, the central control unit 8 can accommodate communication mediums other than IEEE 1394, such as, for example, connections designed for devices such as Stryker Corporation's Integrated Device Network (SIDNE) Control System and Total Performance System (TPS), as well as Stryker Endoscopy's Radio Frequency Ablation System (SERFAS).

In certain embodiments, the central control unit 8 also (or instead) can have one or more "direct" (i.e., non-network) connections 78 to a controlled device 5, as mentioned above and as shown in FIG. 1. In such embodiments, the central control unit 8 includes a communication adapter 70 to couple the microcontroller 71 to the direct connection 78. In certain instances, a direct connection 78 may be implemented as a connection between the central control unit 8 and a device 5 with no other devices or adapters coupled between them, while in other cases, a direct connection 78 may be implemented by connecting the central control unit 8 to a device 5 through a separate, external adapter ("dongle") that emulates the network connection for the central control unit 8.

II. General Operation of the Synchronized Remote Console System

In a given clinical environment, multiple pairs of consoles 9 and central control units 8 may be used in close proximity to each other. This gives rise to the risk of a central control unit 8 responding to control signals from the wrong console 9. To prevent this from occurring, each console 9 is assigned a unique device identifier, such as, for example, the unique ID code of each microcontroller 51. Each central control unit 8 is configured to respond to (i.e., can be "synchronized" with) one or more specific consoles 9, based on their device identifiers. During operation, when a console 9 transmits signals representing user inputs, it transmits its preassigned ID code with those signals. After being synchronized with a specific console 9, the central control unit 8 will ignore any wireless signals it receives which are not accompanied by the correct console ID code (e.g., signals from an unknown or unauthorized console 9). In this manner, the central control unit 8 is prevented from accidentally responding to a wireless console 9 that is in the nearby vicinity but which is not synchronized with the central control unit 8.

According to one embodiment of the invention, synchronization between a wireless console 9 and central control unit 8 is accomplished by means of radio frequency identification (RFID). Specifically, during the manufacturing process, the unique ID code that is assigned to each microcontroller 51 contained within each console 9 is read or obtained. This unique ID code is then written to a RFID chip or tag 27. This newly written RFID tag 27 is then sealed within or mounted upon the console 9 from which the ID code was first obtained.

In order to synchronize the wireless console 9 with the central control unit 8, the console 9 is powered up and brought next to the central control unit 8. More specifically, the area of the console 9 that contains the RFID tag 27 is aligned with the RFID reader 79 on the central control unit 8. The console 9 is then brought in to close proximity (i.e., one inch) to the central control unit 8. Once the RFID tag 27 is close enough, the magnetic field being generated by the RFID reader 79 becomes modulated. The RFID reader 79 detects this specific modulation in the magnetic field and translates it into the unique ID code of that specific console 9.

The RFID reader 79 then transmits the unique ID code of the nearby console 9 to the central control unit's microcontroller 71. At this point, the central control unit 8 becomes synchronized with that specific console 9, and will only act on or acknowledge wireless command signals that are identified by or contain the ID code that is unique to the synchronized wireless console 9.

To alert the user that synchronization between the central control unit 8 and a console 9 has been obtained, the central control unit 8 can be configured to provide an audible or visual cue. Visual cues could be provided on the output indicator 75, or alternatively, provided by a separate "synchronized" indicator (not shown), such as an LED on the central control unit 8 which comes on or changes colors upon obtainment of synchronization.

Once synchronized, the console 9 will be able to control the devices 5 connected to the central control unit 8. However, while the console 9 controls the devices 5 connected to the central control unit 8, the central control unit 8 controls how the console 9 functions. Consider, for example, the foot-controlled console 9 of FIG. 2. When an operator depresses the left pedal 22 of the console 9, the console 9 transmits a generic "left pedal" command signal (encoded with the console's unique ID code) to the central control unit 8. Upon receiving the "left pedal" command signal from console 9, the central control unit 8 first looks for the unique ID code of the console 9 to verify that the received command signal is valid. If valid, the central control unit 8 then compares the received "left pedal" command signal to previously programmed instructions to determine how that specific command signal from the console 9 should be interpreted with respect to the device 5 currently being controlled. The central control unit 8 then issues the interpreted command over the common wired communication medium 6 or direct connection 78 to the device 5 being controlled.

As previously discussed, the central control unit 8 can connect to a plurality of devices 5 which can subsequently be controlled by the remote console 9. To select which device 5 is to be controlled by the remote console 9, a "mode" button is provided upon the central control unit 8. Upon the user depressing the mode button, the central control unit 8 toggles through a list of the connected devices 5 from which the operator can then choose. Depending on the type of remote console 9 being utilized, the user may also be able to remotely select which device 5 is to be controlled by depressing a mode button located on the console 9.

According to another embodiment of the invention, the central control unit 8 is configured to not immediately respond to commands it receives from a synchronized console 9 if a specified period of time (i.e., 30 seconds) of inactivity has passed. Instead, the central control unit 8 will announce, such as visually by its output indicator 75, which device 5 is currently active with the console 9. Issuance of a second command will then resume in normal operation.

Similarly, a predefined extended period of inactivity, the remote console 9 will enter a "sleep" mode to conserve battery power. The central control unit 8 will subsequently display on its output indicator 75 that the console 9 is in a sleep mode. Depressing one of the buttons and/or switches on the console 9 will wake it up.

Communications between a remote console 9 and central control unit 8 can be disabled by unsynchronizing the two devices. A user manually accomplishes this by depressing and holding in the "mode" button on the central control unit 8 for a brief specified period of time. Once unsynchronized, the remote console 9 will not function again until it is resynchronized with a central control unit 8.

Figure 7:
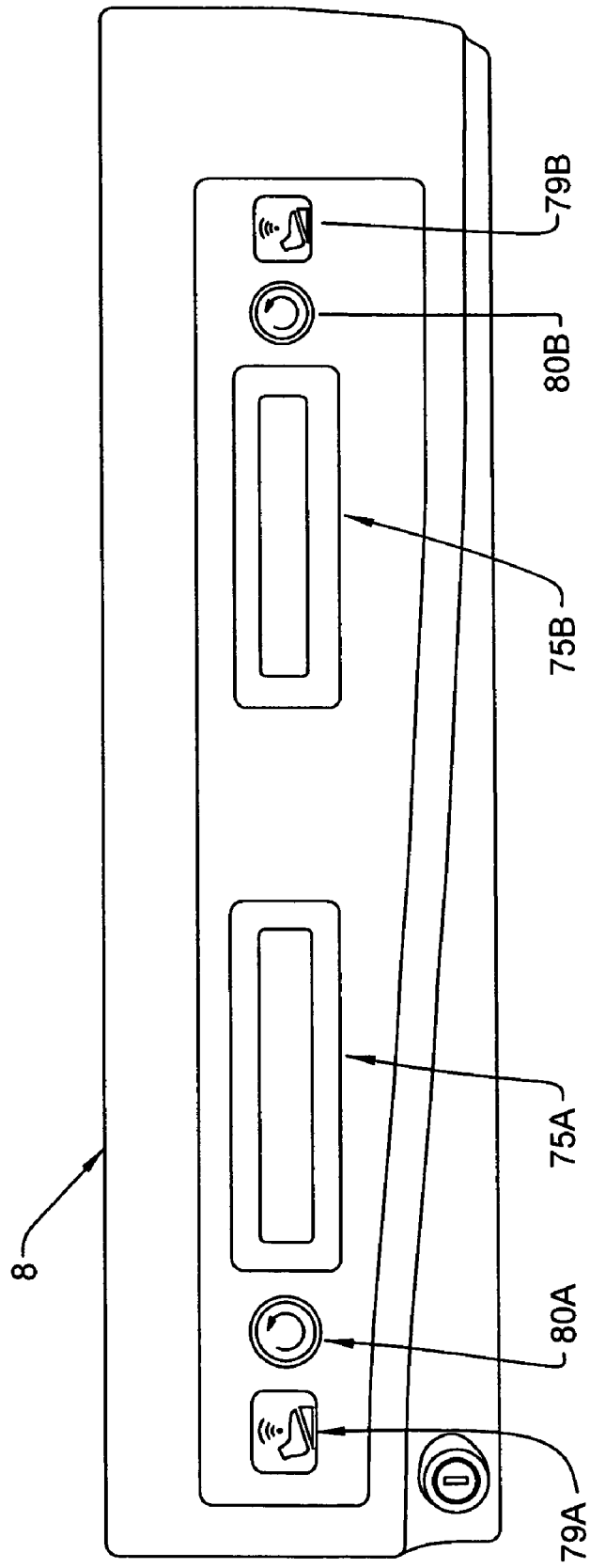
FIG. 7 is an exterior front view of a central control unit capable of synchronizing with two remote consoles according to certain other embodiments of the invention.

According to another embodiment of the invention, the central control unit 8 is capable of being synchronized with two remote consoles 9 at the same time. FIG. 7 is a external front view of one such central control unit 8 capable of synchronizing with two consoles 9. As illustrated, the central control unit 8 of FIG. 7 includes two output indicators 75*a* and 75*b*, two synchronization ports 79*a* and 79*b*, each of which represent a RFID reader, and two "mode" buttons 80*a* and 80*b*.

Besides allowing for two separate synchronizations at the same time, the central control unit 8 as illustrated in FIG. 7 can also be configured to allow the use of two remote consoles (not illustrated) to control the same device 5. This is accomplished by synchronizing a first console, and then placing the central control unit 8 into a "merge" mode by means of its second mode button 80*b*. Once the second console is synchronized, the two consoles are considered merged. When the two consoles are merged, they cannot simultaneously issue commands to the same device 5. Instead, they must alternate controlling the device 5. To alternate control, a user must first stop issuing commands with the first remote console currently in control. The user then presses one of the buttons/pedals/switches on the second remote console. This will cause the central control unit 8 to toggle control to the second console. Repeating the same procedure toggles control back to the first console.

All the embodiments discussed above employed the use of RFID sensors and tags to automatically initiate and carry out the transfer of a remote console's ID code to a central control unit 8, thereby synchronizing the two units and securing the system from accidentally responding to command signals generated by other remote consoles 9 or other wireless devices. However, other embodiments of the present invention are not limited to using RFID tags. These embodiments instead rely on other means to wirelessly convey data, such as an ID code, between a remote console 9 and central control unit 8 when they are brought into close proximity to one another.

For example, one embodiment (not depicted) utilizes optical bar code scanning technology. Specifically, the unique ID code of the remote console 9 is converted into a bar code that is subsequently applied to or affixed to the outer surface of the console 9. A bar code scanner integrated into the central control unit 8, or alternatively, a separate bar code scanner that communicates with the central control unit 8, then scans the remote console's bar code once the console 9 is brought into close enough proximity to the central control unit 8.

Alternatively, additional embodiments may utilize other optical-based methods to convey data between a console 9 and central control unit 8. Consider, for example, a synchronized remote control system according to an additional embodiment (not depicted) that uses an infra-red (IR) transmitter in the remote console 9, and an IR receiver in the central control unit 8. When brought into close proximity to one another, the console's ID code, encoded as an IR signal, is projected onto the IR receiver of the central control unit 8.

Beyond electromagnetic-based conveying means, further embodiments (not depicted) may utilize an acoustic-based system to convey an ID code or other data from the console 9 to the central control unit 8. For example, the remote console 9 could incorporate a small speaker that relays information to the microphone of a central control unit 8, much in the same way as computer modems communicate with one another.

Lastly, the embodiments discussed above primarily focus on using the underlying principles of the present invention to establish a synchronized or secure wireless connection between a remote console 9 and a central control unit 8, thereby providing a user with the means to control one or more devices remotely using a secure and reliable wireless connection. However, in accordance with a further embodiment of the invention, the principles disclosed above are utilized not to establish a secure wireless connection for the transmission of control signals from a remote control, but are instead modified to provide a secure and reliable wireless connection for the simple purpose of transporting raw data from one device to another. In this manner, the wireless connection established by the present invention is utilized as a secure wireless conduit between two devices.

Consider, for example, utilizing the principles of the present invention to establish a secure wireless data path between a wireless video camera and digital recorder, thereby assuring reliable, wireless transport of data between the two devices. Similarly, the concepts of the present invention can be utilized to establish a secure wireless link between any two wireless devices, such as, for example, a wireless head-mounted display unit and its associated computer system which generates real-time video images that are to be projected upon the display.

III. Wireless Protocol, Packet Types, and Signal Timing

In the previous embodiments, secure communication between a remote console 9 and central control unit 8 was solely established by means of a unique ID code passed from the console 9 to the central control unit 8. However, according to additional embodiments, even greater security and reliability is achieved through Applicants' development of a proprietary WUF communication protocol that utilizes specific wireless communication protocols, packet structures, and signal timing.

For illustrative purposes, consider the following exemplary embodiment of a synchronized wireless remote control system which communicates "synchronization" data within the 2.4 GHz frequency band using a Cypress Wireless-USB chipset. Cypress WUSB employs a CDMA-based low-level protocol which encodes each transmitted bit with a 32-bit password (PNCode). On top of this is built an additional proprietary protocol that further protects the data transmission with a 32-bit identifier code, along with a 1-byte checksum capable of restoring a packet with up to 10% of it's data in error. A transmitted packet is accepted and processed only if it contains the correct PNCode, the correct identifier code, and a proper checksum. Lastly, the protocol is strictly time monitored, so in the case of a protocol failure the device will always be put into a safe state.

Note—For a definition of terms used in this section, see the table illustrated in FIG. 8.

To assure patient safety, Applicants developed a secure wireless communication path having low latency and high reliability. This was accomplished by taking a multi-faceted approach that focused not only on the Cypress WUSB CDMA low-level protocol, but also the importance of the PNCode, the structure of a data packet, the types of packets and how they are used, the protocol states, and the timing structure of the signal.

A. The Cypress WUSB CDMA Low-Level Protocol

The Cypress WUSB chipset encodes and decodes its data using a code division multiple access (CDMA) low-level protocol. In short, CDMA requires that a 32-bit code (called a PNCode) be sent for every "1" transmitted, and the inverse of that code be sent for every "0" transmitted. Only if the code, or the inverse of that code, is received with less than two errors (called the threshold) will a valid "1" or "0" be recorded. If the threshold is exceeded, the received bit is marked invalid. Setting the threshold at 2 gives a high level of security to the transmission, while still allowing for a fair amount of noise to be present on the channel.

Additionally, sixteen PNCodes are available on each of the 80 WUSB channels. Each WUF receiver determines the PNCode it will communicate with based on an internal identification number.

Furthermore, the reception of data is 2× oversampled, thereby allowing for operation within a noisy environment.

B. Packet Structure

Figure 9:
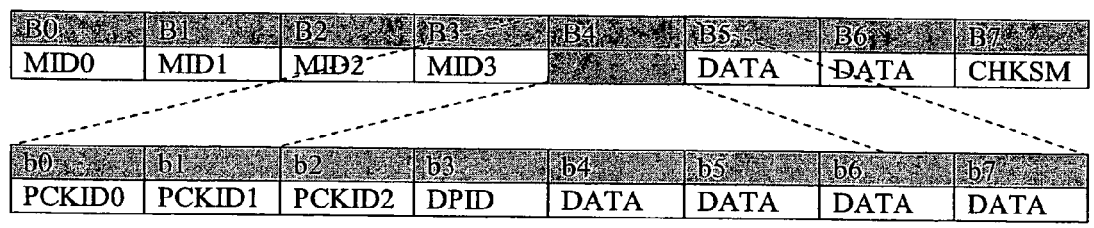
FIG. 9 illustrates the structure of a data packet in accordance with certain embodiments of the invention.

Each packet utilized by the WUF Protocol of the current embodiment is made up of 8 bytes. FIG. 9 shows the structure of each data packet.

Packets B0-B3 contains the Manufacturer's Identification Number (MID) of the transceiver for which the packet is intended. Each Cypress WUSB transceiver chip contains a unique 32-bit MID, i.e. each remote console 9 and central control unit 8 have a unique MID. Only if the received packet's MID matches the MID stored within the Cypress WUSB transceiver chip of the receiver will the packet be accepted as valid.

Packet B4, bits 0-2 (b0-b2), contain the Packet Identifier (PCKID), described in detail in the next section. Bit 3 (b3) of packet B4 contains the data path identifier (DPID), which denotes which data path is being used. Bits 4-7 (b4-b7) of packet B4 contain data (DATA) specific to the packet type.

Packets B5 and B6 also contain data (DATA) specific to the packet type.

Packet B7 contains the packet checksum (CHKSM).

Of special note is the last byte in the packet, the Checksum byte. The Checksum byte allows the receiver to correct up to 1 bit error per byte, or, in other words, to restore a packet to its proper value when up to 10% of its data has been marked as invalid.

C. Packet Types

The protocol employed by the secure remote control system of the present embodiment utilizes 8 different packet identifiers (PCKIDs), including 3 sent by the remote console 9 to the central control unit 8, and 5 sent from the central control unit 8 to the remote console 9. See the table illustrated in FIG. 10, which describes each PCKID, what it is used for, and what specific data it contains.

D. Protocol States

The protocol employed by the secure remote control system of the present embodiment utilizes three different states to describe the connection status between a footswitch and the receiver: NOT BOUND, BOUND, WAS BOUND.

NOT BOUND: A remote console 9 is NOT BOUND if it has not been connected to any central control unit 8 since it was powered up. The footswitch is constantly searching all 80

WUSB channels, looking for a base station bind 1 packet (BS_bind1) transmission from a WUF receiver. Upon receiving a valid BS_bind 1 packet, the console 9 and central control unit 8 go through the binding procedure, shown in the table of FIG. 11. If that procedure is successful, the console 9 moves to the BOUND state.

BOUND: During the BOUND state, the remote console 9 reports its current state every 20-100 ms depending on whether the console 9 has detected a change in the pedal and switch states, or if it has detected a low-battery condition. The table in FIG. 12 shows the BOUND communication between the remote console 9 and central control unit 8.

WAS BOUND: If the remote console 9 loses communication with the central control unit 8, due to interference, an out of range condition, or if the central control unit 8 is turned off, the console 9 enters the WAS BOUND state. During this state, the console 9 searches all 80 WUSB channels, looking for a valid base station acknowledgement packet (BS_ACK) or base station bind 1 packet (BS_bind1). If the console 9 receives a BS_ACK, it begins transmitting to the central control unit 8 that it was previously bound to. If the console 9 receives a BS_bind1, it erases all current bind information, and binds to the new central control unit 8 from which the BS_bind1 packet was received. The table of FIG. 13 shows the WAS BOUND rebinding procedure.

E. Timing

Figure 14:
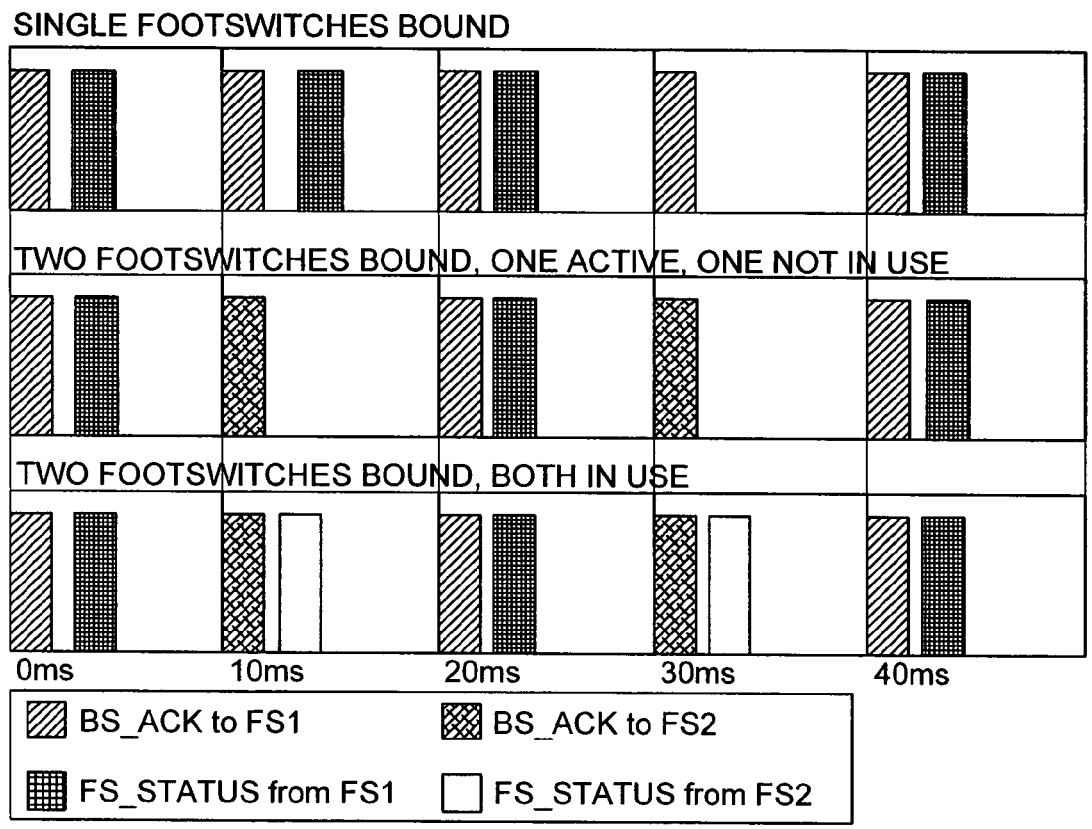
FIG. 14 illustrates several packet timing diagrams according to a further embodiment of the invention.

The communication protocol utilized in the present embodiment is designed for minimal latency and maximum security. Strict timing requirements are employed to provide both of the before mentioned traits. Timing is dictated by the central control unit 8, since in all states the central control unit 8 initiates the communication. Specifically, during the BOUND state, when the remote consoles 9 are reporting their current status, timing becomes very important. Consoles 9 are polled for data every 20 ms. In order to conserve battery power, the consoles 9 are required to respond with their current state whenever they detect a change in their pedal and switch state, or every 100 ms, whichever comes first. Consoles 9 are polled in an alternating structure, for example, a first console is polled, then a second console is polled, etc. FIG. 14 illustrates several packet timing diagrams.

Timing checks are also present to validate the state of the communication path between the console or consoles 9 and the central control unit 8. If a central control unit 8 does not receive communication from a console 9 within a set amount of time, the data path is declared invalid, the controlled device 5 is put into a safe state, and the central control unit 8 enters the WAS BOUND state for that console data path.

Thus, a wireless remote control apparatus that synchronizes with and securely and reliably controls one or more medical devices during a medical procedure has been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A system for controlling at least two medical devices by a secure wireless connection, comprising:

a remote console having at least two user-operable controls and configured to wirelessly transmit console command signals with an identification code unique to the remote console for selecting one of the medical devices and for actuating the selected medical device;

an identification device associated with the remote console and programmed with the identification code with which the identification device is associated;

a central controller in communication with both of the medical devices and controlling at least one of said medical devices in response to the console command signals wirelessly transmitted by the remote console; and an identification reader associated with the central controller which places the central controller and the remote console in a synchronized state when the remote console is brought within a predetermined distance of the central controller so as to permit the identification reader to wirelessly retrieve the identification code programmed in the identification device, wherein the central controller processes console command signals associated with the identification code that corresponds to the remote console with which the central controller is synchronized, and wherein the central controller is configured to detect the connection of said at least two medical devices thereto.

2. The system according to claim 1, wherein the identification device associated with the remote console comprises one of a RFID tag and a barcode, the identification device providing the identification code to the identification reader.

3. The system according to claim 1, wherein the console command signals comprise generic control signals that the central controller subsequently translates into device control signals having a specified format and protocol compatible with the selected medical device being controlled.

4. The system according to claim 1, wherein the remote console comprises a first remote console and the system further includes a second remote console having a second identification device with a second identification code that is provided to the identification reader, wherein the first and second remote consoles are both synchronized with the central controller, and both the first and the second console are configured to operate the at least two medical devices.

5. The system according to claim 4, wherein the first synchronized remote console and the second synchronized remote console are configured to control the same medical device.

6. A system for controlling at least two medical devices by a secure wireless connection, comprising:

a remote console having a first user-operable control and a second user-operable control, the remote console being configured to wirelessly transmit console command signals with an identification code unique to the remote console for selecting one of the medical devices and for actuating the selected medical device;

an identification device associated with the remote console and programmed with the identification code with which the identification device is associated;

a central controller in communication with both of the medical devices and controlling a first one of said medical devices in response to console command signals from the first control, and the central controller controlling a second one of said medical devices in response to console command signals from the second control; and an identification reader associated with the central controller which places the central controller and the remote console in a synchronized state when the remote console is brought within a predetermined distance of the central controller so as to permit the identification reader to wirelessly retrieve the identification code programmed in the identification device, wherein the central controller processes console command signals associated with the identification code that corresponds to the remote console with which the central controller is synchronized.

7. The system according to claim 1, wherein the system is configured for the user to select the medical device to control from the at least two medical devices in communication with the central controller by repeated activation of one of the at least two user-operable controls to cycle between available ones of the at least two medical devices.

8. A system for controlling at least two medical devices by a secure wireless connection, comprising:
   a remote console having at least two user-operable controls and configured to wirelessly transmit console command signals with an identification code unique to the remote console for selecting one of the medical devices and for actuating the selected medical device;
   an identification device associated with the remote console and programmed with the identification code with which the identification device is associated;
   a central controller in communication with both of the medical devices and controlling at least one of said medical devices in response to the console command signals wirelessly transmitted by the remote console; and
   an identification reader associated with the central controller which places the central controller and the remote console in a synchronized state when the remote console is brought within a predetermined distance of the central controller so as to permit the identification reader to wirelessly retrieve the identification code programmed in the identification device,
   wherein the central controller processes console command signals associated with the identification code that corresponds to the remote console with which the central controller is synchronized, and
   wherein said at least two medical devices connect to the central controller by a direct connection or by a common wired communication medium.

9. The system according to claim 1, wherein the remote console and the central controller communicate with one another using one of infrared and laser.

10. The system according to claim 1, wherein the central controller further comprises at least one of a visual indicator and an audible indicator to indicate which one of the two medical devices is selected.

11. The system according to claim 1, wherein the remote console comprises a footswitch.

12. The system according to claim 1, wherein the central controller is configured for initiating all wireless communication with the synchronized remote console by polling the synchronized remote console at a predefined interval of. time.

13. The system according to claim 12, wherein the central controller is configured to provide the controlled medical device with a non-operating state if the central controller fails to receive a valid wireless communication from the synchronized remote console in control of the medical device within a predetermined amount of time.

14. A method of controlling at least two medical devices by a secure wireless connection, comprising the steps of:
   providing a remote console including an identification device which is programmed with a unique identification code unique to the remote console and having at least one user-operable control for remotely controlling at least one function of at least one of said two medical devices;
   connecting the at least two medical devices to a central controller capable of communicating wirelessly with the remote console, the central controller including a transmitter, a receiver and an identification reader;
   wirelessly synchronizing the remote console with the central controller by placing the remote console within a predetermined distance of the identification reader to wirelessly retrieve the identification code from the identification device with the identification reader regardless of the remote console providing a wireless remote console command signal and independently of the transmitter and the receiver of the central controller;
   generating with the synchronized remote console at least one wireless remote console command signal that is indicative of a state of the at least one user-operable control and which includes the identification code unique to that remote console; and
   preventing the central controller from processing any other wireless remote console control signals unless the control signals include the identification code that is unique to the remote console that is synchronized with the central controller.

15. The method according to claim 14, wherein the wireless control signals generated by the remote console are generic control signals that the central controller subsequently translates into device control signals having a specified format and protocol compatible with the selected medical device being controlled.

16. The method according to claim 14, the remote console comprising a first remote console, and further comprising the steps of:
   providing a second remote console; and
   wirelessly synchronizing the second remote console with the central controller after the first remote console has been synchronized with the central controller so that the first and second remote consoles are capable of controlling the same selected medical device concurrently.

17. The method according to claim 14, wherein the at least one user-operable control comprises a first control and a second control associated with the remote console, and further comprising the steps of:
   controlling a first medical device in communication with the central controller with the first control of the remote console; and
   controlling a second medical device in communication with the central controller with the second control of the remote console.

18. The method according to claim 14, further comprising the step of selecting a medical device to control from a plurality of medical devices in communication with the central controller by cycling between available medical devices in communication with the central controller by repeatedly activating the at least one user-operable control of the remote console.

19. A system for controlling at least one medical device by a secure wireless connection, comprising:
   a remote console having at least one user-operable control and configured to wirelessly transmit console command signals indicating a state of the at least one user-operable control and an identification code unique to the remote console;
   an identification device associated with the remote console and programmed with the identification code with which the identification device is associated;

a central controller in communication with and controlling at least one medical device in response to console command signals wirelessly transmitted by the remote console; and an identification reader associated with the central controller which places the central controller and the remote console in a synchronized state when the remote console is brought within a predetermined distance of the central controller so as to permit the identification reader to wirelessly retrieve the identification code programmed in the identification device, wherein the identification reader is configured for communicating with the identification device separately and independently of the communication between the central controller and the remote console;

wherein the central controller will only process console command signals associated with the identification code that corresponds to the remote console with which the central controller is synchronized.

20. A system for controlling at least one medical device by a secure wireless connection, comprising:

a wireless remote console having at least one user-operable control and configured to wirelessly transmit console command signals indicating a state of the at least one user-operable control and an identification code unique to the remote console;

an identification device associated with the remote console and programmed with the identification code unique to the remote console;

a central controller in communication with and controlling the at least one medical device in response to console command signals wirelessly transmitted by the remote console, the central controller including a transceiver for receiving the unique identification code and the console command signals from the remote console; and an identification reader associated with the central controller for automatically placing the central controller and the remote console in a synchronized state when the remote console is brought within a predetermined distance of the identification reader, which enables the identification reader to retrieve the unique identification code from the identification device independently of the transceiver, wherein the central controller is configured to process console command signals associated with the identification code that corresponds to the remote console after the central controller is synchronized with the remote console by the identification reader retrieving the identification code from the identification device independently of the transceiver, the console command signals controlling actuation of the at least one medical device.

21. The system according to claim 20, the remote console comprising a first remote console and the identification code comprises a first unique identification code, the system further comprising a second remote console including a second identification device with a second unique identification code, wherein the identification reader places the central controller and the second remote console in a synchronized state when the second remote console is brought within a predetermined distance of the identification reader, which enables the identification reader to wirelessly retrieve the second identification code from the second identification device independently of the transceiver.

22. A method of controlling at least two medical devices by a secure wireless connection, comprising the steps of:

providing a remote console associated with a unique identification code, said remote console having at least one user-operable control for remotely controlling at least one function on at least one of the two medical devices and an identification device storing the unique identification code;

connecting the at least two medical devices to a central controller capable of communicating wirelessly with the remote console, the central controller including a transmitter, a receiver and an identification reader not in communication with the receiver;

detecting with the central controller the at least two medical devices connected thereto;

wirelessly synchronizing the remote console with the central controller by placing the remote console within a predetermined distance of the central controller so that the identification reader reads the identification code from the identification device;

generating with the synchronized remote console at least one wireless remote console command signal that is indicative of a state of the at least one user-operable control and which includes the identification code unique to that remote console;

maintaining in the central controller knowledge of the at least two medical devices for selective operation thereof; and preventing the central controller from processing any other wireless remote console control signals unless the control signals include the identification code that is unique to the remote console that is synchronized with the central controller.

23. The method according to claim 22, wherein the remote console is free from knowledge of the medical device selected for operation.

24. The method according to claim 22, including the step of the central controller communicating which of the at least two medical devices is selected for control by at least one of visual indicators and an audible indicator.

25. A system for controlling at least two medical devices by a secure wireless connection, comprising:

a remote console having at least two user-operable controls and configured to wirelessly transmit console command signals with an identification code unique to the remote console for selecting one of the medical devices and for actuating the selected medical device;

an identification device associated with the remote console and programmed with the identification code with which the identification device is associated;

a central controller in communication with both of the medical devices and controlling at least one of said medical devices in response to the console command signals wirelessly transmitted by the remote console, the central controller storing knowledge of said at least two medical devices for translating the console control signals into control signals having a format and protocol for recognition by the at least two said medical devices; and an identification reader associated with the central controller which places the central controller and the remote console in a synchronized state when the remote console is brought within a predetermined distance of the central controller so as to permit the identification reader to wirelessly retrieve the identification code programmed in the identification device, wherein the central controller processes console command signals associated with the identification code that corresponds to the remote console with which the central controller is synchronized.

26. The system according to claim 25, wherein the remote console is free from medical device identification codes.

27. A system for controlling at least two medical devices by a secure wireless connection, comprising:
- a remote console having at least two user-operable controls and configured to wirelessly transmit console command signals with an identification code unique to the remote console for selecting one of the medical devices and for actuating the selected medical device;
- an identification device associated with the remote console and programmed with the identification code with which the identification device is associated;
- a central controller in communication with both of the medical devices and configured to selectively control both of the at least two medical devices in response to the console command signals wirelessly transmitted by the remote console; and
- an identification reader associated with the central controller which places the central controller and the remote console in a synchronized state when the remote console is brought within a predetermined distance of the central controller so as to permit the identification reader to wirelessly retrieve the identification code programmed in the identification device,
- wherein the central controller processes console command signals associated with the identification code that corresponds to the remote console with which the central controller is synchronized.

* * * * *

UNITED STATES PATENT AND TRADEMARK OFFICE
CERTIFICATE OF CORRECTION

| | | |
|---|---|---|
| PATENT NO. | : 7,846,150 B2 | Page 1 of 1 |
| APPLICATION NO. | : 11/263083 | |
| DATED | : December 7, 2010 | |
| INVENTOR(S) | : Andrew J. Hamel et al. | |

It is certified that error appears in the above-identified patent and that said Letters Patent is hereby corrected as shown below:

Please delete the first "." appearing in the last line of Claim 12 at column 13, line 53.

Signed and Sealed this
Fifteenth Day of February, 2011

David J. Kappos
*Director of the United States Patent and Trademark Office*